United States Patent [19]

Ma et al.

[11] Patent Number: 5,770,083

[45] Date of Patent: *Jun. 23, 1998

[54] SEPARATION OF POLAR COMPOUNDS BY AFFINITY COUNTERCURRENT CHROMATOGRAPHY

[75] Inventors: Ying Ma, Rockville; Yoichiro Ito, Bethesda, both of Md.

[73] Assignee: The United States of America as represented by the Department of Health and Human Services, Washington, D.C.

[*] Notice: The term of this patent shall not extend beyond the expiration date of Pat. No. 5,354,473.

[21] Appl. No.: 514,917

[22] Filed: Aug. 14, 1995

[51] Int. Cl.$^6$ .................................................. B01D 15/08
[52] U.S. Cl. ........................ 210/635; 210/657; 210/198.2
[58] Field of Search ................................... 210/635, 656, 210/657, 659, 198.2

[56] References Cited

U.S. PATENT DOCUMENTS

| | | | |
|---|---|---|---|
| 4,414,108 | 11/1983 | Ito | 210/198.2 |
| 4,430,216 | 2/1984 | Ito | 210/198.2 |
| 4,615,805 | 10/1986 | Ito | 210/657 |
| 4,849,110 | 7/1989 | Takata et al. | 210/198.2 |
| 5,114,589 | 5/1992 | Shibusawa et al. | 210/657 |
| 5,169,521 | 12/1992 | Oka et al. | 210/198.2 |
| 5,169,984 | 12/1992 | Cahnmann et al. | 562/447 |
| 5,215,664 | 6/1993 | Kitazume et al. | 210/635 |
| 5,217,608 | 6/1993 | Conway | 210/198.2 |
| 5,256,293 | 10/1993 | Pirkle | 210/198.2 |
| 5,273,656 | 12/1993 | Anderson | 210/635 |
| 5,290,440 | 3/1994 | Pirkle | 210/198.2 |
| 5,332,504 | 7/1994 | Ito et al. | 210/635 |
| 5,354,473 | 10/1994 | Ito et al. | 210/635 |
| 5,449,461 | 9/1995 | Ito | 210/635 |

OTHER PUBLICATIONS

Ito, Yoichiro, "Cross–Axis Synchronous Flow–Through Coil Planet Centrifuge Free of Rotary Seals for Preparative Countercurrent Chromatography. Part 1. Apparatus and Analysis of Acceleration," *Separation Science and Technology*, 22(8–10):1971–1987 (1987).

Ito, Yoichiro, Cross–Axis Synchronous Flow–Through Coil Planet Centrifuge Free of Rotary Seals for Preparative Countercurrent Chromatography. II. Studies on Phase Distribution and Partition Efficiency in Coaxial Coils, *Separation Science and Technology*, 22(8–10):1989–2009 (1987).

Ito, Y., et al., "Cross–Axis Synchronous Flow–Through Coil Planet Centrifuge for Large–Scale Preparative Counter–Current Chromatography. I. Apparatus and Studies on Stationary Phase Retention in Short Coils," *J. of Chromatography*, 449:135–151 (1988).

Ito, Y., et al., "Cross–Axis Synchronous Flow–Through Coil Planet Centrifuge for Large–Scale Preparative Counter–Current Chromatography. II. Studies in Partition Efficiency in Short Coils and Preparative Separations with Multilayer Coils," *J. of Chromatography*, 449:153–164 (1988).

Ito, Y., et al., "Cross–Axis Synchronous Flow–Through Coil Planet Centrifuge for Large–Scale Preparative Counter–Current Chromatography. III. Performance of Large–Bore Coils in Slow Planetary Motion," *J. of Chromatography*, 449:151–162.

(List continued on next page.)

*Primary Examiner*—Ernest G. Therkorn
*Attorney, Agent, or Firm*—Townsend and Townsend and Crew LLP

[57] ABSTRACT

Separations of very hydrophilic organic compounds has now been achieved using countercurrent chromatography in which a ligand for the analytes of interest is used to enhance the partitioning of the polar species into the organic layer of an aqueous/organic solvent mixture. The compounds are separated according to their affinity for the ligand in the stationary organic phase. This method of affinity countercurrent chromatography can also be conducted in a pH-zone refining mode.

9 Claims, 5 Drawing Sheets

OTHER PUBLICATIONS

Ito, Y., et al., "Improved high–speed counter–current chromatograph with three multilayer coils connected in series. IV. Evaluation of preparative capability with large multilayer coils," *J. of Chromatography*, 538:22–26 (1991).

Ito, Y., et al., "Cross–axis synchronous flow–through coil planet centrifuge (Type XLL) I. Design of the apparatus and studies on retention of stationary phase," *J. of Chromatography*, 538:59–66 (1991).

Ito, Yoichiro, "High–Speed Countercurrent Chromatography," *CRC Critical Reviews in Analytical Chemistry*, 17(1):65–143 (1986).

Ito, Yoichiro, "High–Speed Countercurrent Chromatography," *Nature*, 326(6111):419–420 (26 Mar. 1987).

Conway, Walter D., *Countercurrent Chromatography*, VCH Publishers, Inc., New York, pp. 1–115 (1990).

Cahnmann H.J., et al., "Synthesis and characterization of N–bromoacetyl–3,3',5–triiodo–L–thyronine," *J. of Chromatography*, 538:165–175 (1991).

Weisz, A., et al., "Complementary use of counter–current chromatography and preparative reversed–phase high–performance liquid chromatography in the separation of a synthetic mixture of brominated tetrachlorofluoresceins," *J. of Chromatography*, 607:47–53 (1992).

Oliveros, L., et al., "Donor–Acceptor Chiral Centrifugal Partition Chromatography: Complete Resolution of Two Pairs of Amino–Acid Derivatives with a Chiral II Donor Selector," *J. Liquid Chromatography*, 17(11):2301–2318 (1994).

Pirkle, W.H., et al., "Use of Intercalative Effects to Enhance Enantioselectivity," *J. Chromatogr.*, 641:11–19 (1993).

Weisz, A., et al., "New Preparative–Scale Purification Techniques: pH–Zone–Refining Countercurrent Chromatography," *J. Am. Chem. Soc.*, 116:704–708 (1994).

Oka, F., et al., "Systematic search for suitable two–phase solvent systems for high–speed counter–current chromatography," *J. Chromatography*, 538:99–108 (1991).

Ito, Y., "Countercurrent chromatography," *J. Chromatography*, Library, Part A, Chapter 2, (Edited by E. Heftmann) Elsevier Scientific Publishing Company, Amsterdam, Netherlands, pp. A69–A107 (1992).

Kitazume, E., et al., "Separation of rare earth elements by high–speed countercurrent chromatography," *J. Chromatography*, 538:133–140 (1991).

Ma, Y., et al., "Resolution of gram quantities of racemates by high–speed counter–current chromatography," *J. Chromatography A*, 704:75–81 (1995).

Weisz, A., et al., "Preparative separation of polar unstable compounds (catecholamines) from a synthetic mixture by high–speed counter–current chromatography," *J. Chromatography*, 383:132–136 (1986).

Ito, Y, et al., "pH–Zone–refining counter–current chromatography," *Modern Countercurrent Chromatography*, W.D. Conway and R.J. Petroski (Editors), ACS Symposium Series 593, American Chemical Society, Washington, D.C., Chapter 14, pp. 156–183 (1995).

Scher, A.L., et al., "Equilibrium Model for pH–Zone–Refining Countercurrent Chromatography," W.D. Conway and R.J. Petroski (Editors), ACS Symposium Series 593, American Chemical Society, Washington, D.C., Chapter 15, pp. 184–202 (1995).

Ying Ma, et al. "Affinity Countercurrent Chromatography Using a Ligand in the Stationary Phase", *Anal Chem.* 68:1207–1211 (1996).

SEPARATION OF POLAR COMPOUNDS BY AFFINITY COUNTERCURRENT CHROMATOGRAPHY

This invention lies in the field of liquid-liquid partition chromatography, and in particular in the separation of polar compounds using chromatographic techniques.

BACKGROUND OF THE INVENTION

Countercurrent chromatography (CCC) is a form of liquid-liquid partition chromatography which relies on the continuous contact between two immiscible solvents, one of which is mobile relative to the other, in a flow-through tubular column, free of any solid support matrix. The retention time of a solute in the phase contact region of the system is determined by the volume ratio of the solvents, the partition coefficient of the solute between the solvents, and the degree of contact between the solvents. Like other forms of liquid-liquid partition chromatography, one of the solvents serves as a carrier, drawing the solutes from the other solvent and carrying the solutes out of the column in the order of elution. This carrier solvent is thus referred to as the mobile phase, while the other solvent is referred to as the stationary phase, even though it is not strictly stationary in many applications of the method. Solvent mixing, retention of the stationary phase in the column, and solute partitioning all take place in the column by the aid of a suitable acceleration field established by gravity, centrifugal force or both, and the configuration of the column.

Most equipment used for CCC separations involves a coil of column tubing, a portion of which is filled with the stationary phase while the mobile phase is passed through it. By varying the length and diameter of the tubing, CCC has been used for both analytical and preparative separations.

The flow rate of the mobile phase may be varied by varying the field imposed on the column. Units which operate in the presence of a gravitational field only are restricted to slow flow rates, with the resulting separations typically requiring 1 to 3 days, to avoid displacing the stationary phase. A unit which operates in the presence of a centrifugal acceleration field of 40 g or more allows faster flow rates and permits separation times of only a few hours.

Separations by CCC may be performed using any immiscible pair of solvents, provided that the solvents differ in density to at least a slight degree. Both normal-phase and reverse-phase separations may be performed, with the more polar solvent as the stationary phase for normal-phase separations, and the less polar solvent as the stationary phase for reverse-phase separations.

The operational aspects of CCC are similar to the more conventional liquid-liquid chromatography (LLC). Typically, after the immiscible solvent phases are equilibrated relative to one another, the column is filled with the stationary phase. The sample is then injected into the column and elution with the mobile phase is begun. The centrifuge is then started and the eluting fractions are collected. Initially, the fractions are composed of the stationary phase which is displaced from the column. However, once hydrodynamic equilibrium between the phases is achieved, only small portions of the stationary phase will co-elute with the mobile phase. The effluent is continuously monitored with a uv detector and fractionated into test tubes using a fraction collector. The collected fractions are monitored by any of a variety of means including spectroscopic methods and thin-layer chromatography.

Countercurrent chromatographic theory, as well as apparatus for performing the method, are described by Ito, Y., in "Principle and Instrumentation of Countercurrent Chromatography, " in *Countercurrent Chromatography: Theory and Practice* Mandava, N. B., and Ito, Y., eds., pp. 79–442 (Marcel Dekker, New York, 1988) and by Conway, W. D., in *Countercurrent Chromatography: Apparatus, Theory and Applications* (VCH, New York, 1990). Most countercurrent chromatographs use a column which is formed into a helical coil. This coil is in turn mounted onto a column holder in various configurations relative to the means for rotating it and relative to the acceleration field that acts on it.

Each column and each type of rotation produce different types of mixing between the solvent phases and are particularly suited for specific separations. However, certain disadvantages to CCC exist.

One disadvantage associated with CCC is the increased peak width associated with increased retention time of the solute. This increased peak width makes detection of the solute more difficult, and requires a larger volume of eluate to be collected and processed in order to obtain a maximum yield of solute. This disadvantage is particularly acute when preparative separations are desired. Nevertheless, increased retention time is desirable in order to avoid co-eluting impurities with the solute. Commonly-owned, co-pending U.S. patent application Ser. No. 07/946,613, filed Sep. 18, 1992, discloses a method for obtaining sharp elution peaks in analytical or semi-preparative CCC without decreasing the retention time of the solute, by adding a peak sharpening agent to either the stationary phase or the sample mixture. When acidic compounds are to be separated, the peak sharpening agent is an acid. When basic solutes are to be separated, the peak sharpening agent is a base.

More recently, an unusually efficient separation of mixtures of acids or bases has been described using a unique modification of the techniques of countercurrent chromatography. See, Ito, et al. U.S. Pat. No. 5,332,504, the disclosure of which is incorporated herein by reference. According to this modification, the two immiscible liquid solutions which are to serve as the stationary and mobile phases, respectively, are modified prior to the performance of the separation by rendering one of the phases acidic and the other basic. Separation of a mixture of acids is then performed in a system in which the acidified solution serves as the stationary phase and the basified solution as the mobile phase. Conversely, separation of a mixture of bases is performed in a system in which the basified solution serves as the stationary phase and the acidified solution as the mobile phase. Individual acid or basic solutes separated by this method elute in contiguous, well-resolved, rectangularly shaped peaks, the solutes eluting in order of their $pK_a$ values and hydrophobicity and the fractions within any single peak being of substantially constant concentration. The combined fractions within each peak differ in pH, successively increasing in the case of a basic mobile phase and successively decreasing in the case of an acidic mobile phase. For this reason, the technique has been referred to as "pH-zone-refining countercurrent chromatography."

A recent modification of pH-zone-refining countercurrent chromatography is carried out in a manner analogous to displacement chromatography. See, commonly-owned, co-pending U.S. patent application Ser. No. 08/263,924, filed Jun. 21, 1994 and incorporated herein by reference. This method uses a retainer base (acid) in the stationary phase to retain analytes in the column and a displacer acid (base) to elute the analytes in the decreasing (or increasing) order of $pK_a$ and hydrophobicity. The elution produces a train of highly concentrated rectangular solute peaks with minimum overlap. To use pH-zone-refining CCC in a displacement mode, the mobile and stationary phases are switched. Thus, the original eluent becomes a retainer to retain analytes in the stationary phase, and the original retainer acid becomes a displacer to displace the analytes from the stationary phase to the mobile phase at the back of the solute bands.

Displacement countercurrent chromatography and pH-zone-refining countercurrent chromatography (in the normal mode) both entail certain advantages over previously known counter-current chromatography techniques. First, the method permits one to load the sample as a suspension into the separation column. Thus, mixtures of compounds that are only partially soluble in the solvent system can be separated efficiently. In addition, the lack or small degree of elution peak overlap permits one to separate mixtures of greater volume than before in any given column without loss of resolution. For example, columns which are otherwise recommended for separations of mixtures of a certain maximum size can be used for separating mixtures up to ten times that size or greater. Likewise, mixtures containing higher concentrations of the acid or basic solutes can be separated with no loss in resolution. As the concentration of solute increases, the separation simply produces a wider plateau for each solute.

Most recently, methods have been reported for the chiral separation of enantiomeric compounds using high-speed countercurrent chromatography (see co-pending application, U.S. Ser. No. 08/357,845, incorporated herein by reference). In these methods, the separations are carried out with a two-phase solvent system in which a chiral selector is distributed almost exclusively in the stationary phase while the analytes are partitioned between the two phases. The column is first filled with the stationary phase containing the chiral selector, followed by sample injection. The mobile phase is then eluted through the column. A racemic mixture of enantiomers is resolved according to the difference in affinities of the D- and L-forms (or (+) and (−) forms) to the chiral selector. As is a common practice in high performance liquid chromatography (HPLC), the CCC separation can be repeated by successive sample injection without renewing the column contents. The liquid stationary phase can hold a large amount of the chiral selector compared to a solid support chiral stationary phase within the conventional chromatographic column. The sample loading capacity and resolution of racemates depend not only on the column volume but also on the concentration of the chiral selector in the stationary phase. Consequently, in HSCCC the chiral separation can be applied in both analytical and preparative scales using the same column only by adjusting the concentration of chiral selector in the stationary phase.

Yet another group of analytes which have been difficult to separate using liquid-liquid partition techniques are the polar organic compounds. This group of compounds is typically very water soluble with only slight solubility in organic solvents such as n-butanol, t-butyl methyl ether, hexanes or ethyl acetate. Unfortunately, to achieve separation of related compounds within a group of analytes, the compounds must partition into both aqueous and organic solvent systems. Efforts to optimize the partition coefficient for these compounds have typically involved either changing the relative hydrophobicity of the organic solvent or altering the pH or ionic strength of the solvents for charged analytes. The present invention provides an alternative strategy for the separation of polar organic compounds which are not otherwise amenable to separation by the above methods.

SUMMARY OF THE INVENTION

The present invention provides methods for the preparative-scale separation of polar organic compounds in a mixture using high-speed countercurrent chromatography (HSCCC). In one embodiment, a ligand for the analyte is held in a liquid stationary phase through which a mobile phase flows, the chromatographic process taking place between the two liquid phases. The separations are carried out with a two-phase solvent system in which the chiral selector is distributed almost exclusively in the stationary phase while the analytes are partitioned between the two phases. The column is first filled with the stationary phase containing the ligand, followed by sample injection. The mobile phase is then eluted through the column. A mixture of polar compounds is separated according to the difference in affinities of the individual analytes for the ligand. As is a common practice in high performance liquid chromatography (HPLC), the CCC separation can be repeated by successive sample injection without renewing the column contents. The sample loading capacity and separation of the polar compounds depends not only on the column volume but also on the concentration of the ligand in the stationary phase. The present invention also provides methods for the preparative-scale separation of polar organic compounds in a mixture using affinity countercurrent chromatography run in the pH-zone-refining mode.

BRIEF DESCRIPTION OF THE DRAWINGS

FIG. 1 shows two HPLC chromatograms from separations of four DNB-amino acid racemates using affinity HSCCC.

In FIG. 1B, DPA was added to the stationary phase as a ligand.

In FIG. 1B, DEHPA (di-(2-ethylhexyl)phosphoric acid) was added to the stationary phase as a ligand.

In FIG. 1B, DEHPA was added to the stationary phase as a ligand (1.5% v/v).

DETAILED DESCRIPTION OF THE INVENTION

The following abbreviations are used herein: Ala, alanine; DEHPA, di-(2-ethylhexyl)phosphoric acid; DPA, N-dodecanoyl-L-proline-3,5-dimethylanilide; DOPA, 3,4-dihydroxyphenylalanine; DNB, dinitrobenzoyl; HPLC, high performance liquid chromatography; DNP, dinitrophenyl; Glu, glutamic acid; Gly, glycine; HSCCC, high-speed countercurrent chromatography; I.D., inside diameter; Leu, leucine; MBE, methyl t-butyl ether; Orn, ornithine; Phe, phenylalanine; Phg, phenylglycine; Pro, proline; PTFE, polytetrafluoroethylene; TLC, thin layer chromatography; Trp, tryptophan; Tyr, tyrosine; and Val, valine.

As used herein, the term "ligand" is used to refer to a compound which itself partitions more favorably into organic solvents and which interacts with members of a mixture of polar organic compounds to enhance the solubility of the polar organic compounds in an organic solvent system.

As used herein, the term "separating" means to increase the amount of one component relative to the amounts of other components in a sample mixture. The mixture produced upon "separating" one component will be substantially free from the other components in the sample mixture, but may contain added quantities of solvents.

As used herein, the phrase "immiscible liquid phases" refers to liquids which may be partially miscible, but which separate into two phases having a liquid interface on standing. Typically, the two phases will comprise an organic phase and an aqueous phase. Suitable organic solvents include butanol, diethyl ether, hexane, ethyl acetate, methanol, methyl t-butyl ether, and acetonitrile.

As used herein, the term "identifying" means determining by spectroscopic means such as UV detection, refractive index detection, mass spectroscopy, and IR detection whether the desired compound is present in a particular sample or eluted fraction. Compounds may also be "identified" by a comparison of their elution times using HPLC.

The method of the present invention utilizes a countercurrent chromatographic centrifuge which may be any of the centrifuges generally used in other modes of countercurrent chromatography. A variety of these centrifuges have been described by Ito, Y., in "Principle and Instrumentation of Countercurrent Chromatography," in *Countercurrent Chromatography: Theory and Practice* Mandava, N. B., and Ito, Y., eds., pp. 79–442 (Marcel Dekker, New York, 1988) and by Conway, W. D., in *Countercurrent Chromatography: Apparatus, Theory and Applications* (VCH, New York, 1990).

Countercurrent chromatography utilizes the hydrodynamic behavior of two immiscible solvent phases mixing in a column to effect the separation of a solute from other components in a sample.

For any of the methods of the present invention, any mixture of solvents which forms two phases on standing may be used. The phases may each be independently composed of organic solutions or aqueous solutions. In a preferred embodiment, one phase is composed of one or more organic solvents and the other phase is substantially aqueous. When chromatography is conducted with the aid of a centrifuge, preferred solvents are those which form two phases having a difference in density of at least 0.05 g/mL. The phases may be equilibrated relative to one another either prior to or during chromatography. In those methods using a pH-zone refining mode of affinity CCC, the two phases may be equilibrated prior to acidifying or basifying the separate phases. When a basic aqueous phase is used as a mobile phase for separation of acidic solutes, the phases may be equilibrated after the aqueous phase is made basic. Similarly, when an acidic aqueous phase is used as a mobile phase for the separation of basic solutes, the phases may be equilibrated after the aqueous phase is made acidic. In a preferred embodiment, the phases are equilibrated in their neutral form by shaking them together and then allowing them to separate prior to charging the column with the stationary phase. When the phases are equilibrated in their neutral form, the stationary phase may be acidified (for separation of acidic solutes) or basified (for separation of basic solutes) prior to charging the chromatography column.

The selection of the solvent system for affinity separations using HSCCC is primarily based on the partition coefficients (K) between the two phases of both the ligand and the analyte of interest. Preferably, the ligand will be distributed mainly into the stationary phase, whereas the analytes should have K values of about 0.3 to 10 so that they are rather evenly distributed between the two phases. In one preferred embodiment, the solvent system is composed of hexane, ethyl acetate, methanol and water. More preferably, the solvent system is composed of hexane, ethyl acetate, methanol and 10 mM HCl. In another preferred embodiment, the solvent system is composed of methyl t-butyl ether and water.

The selection of the solvent system for affinity chromatography using pH-zone-refining CCC will be as described in U.S. Pat. No. 5,332,504. Briefly, the degree of acidity and basicity of the two phases is adjusted such that an acidic phase is used having a pH below about 4 and preferably below about 3. Similarly, the basic phase will in most cases have a pH above about 8 and preferably above about 9. The use of a more basic mobile phase will result in shorter elution times for acidic compounds. Similarly, a more acidic mobile phase will reduce the elution times of basic samples.

The motions which are applied to a CCC column are best described as corresponding to a solar system. In particular, a coiled column may undergo rotation about one or more axes. Solar coaxial motion is found when the coiled column is rotated about the axis of the coil. When the coil is mounted with its axis parallel and offset from a second axis, and the column is rotated only about the second axis, the rotation is termed solar satellite or solar eccentric motion. Planetary motion is provided when rotation occurs about two axes. When a coiled column is rotated about its own axis and also rotated about a second parallel axis, the motion is termed planetary coaxial motion. When a coiled column is rotated about a first external axis parallel to the axis of the coiled column, and the first external axis is simultaneously revolving about a second external parallel axis, the motion is termed planetary satellite or planetary eccentric motion.

In addition to configurations having parallel axes, there are also configurations in which the column axis is inclined or skewed relative to the external axes. Another type of planetary motion results when the two axes about which rotation occurs are orthogonal to one another. Methods utilizing this type of configuration are termed cross-axis CCC.

The columns employed in CCC are equally diverse. The majority are helical, but may vary in the material of fabrication, length, width, pitch of its winding, and mounting onto a column holder. Modern columns are typically constructed of polytetrafluoroethylene tubing which is capable of maintaining its shape and integrity while being exposed to a strong acceleration field. The inside diameter of the tubing is typically between 0.75 and 3 mm. While a single-layer coil may involve only a few meters of tubing, a multi-layer coil might contain more than 100 m of the tubing. Columns to be used for analytical purposes typically have an inside diameter which is more narrow and a length which is longer than a column used for preparative purposes. Additionally, helical columns may be either right-handed or left-handed. The handedness of the coils are determined by the direction in which the coils are wound onto a spool-shaped column holder. The helical column may be either a single layer or multilayer coil. For another column shape, the tubing may be wound onto a flexible core which is in turn coiled onto the column holder to produce a toroidal coil. Yet another type of column is a single layer spiral in which the tubing is wound in one layer onto a core and upon itself. The columns are further equipped with flow tubes which provide for the introduction of sample and mobile phases using an external pump. The tubes further allow the eluate to be collected using an automated fraction collector.

The present invention can be used with any of the columns and motions employed for CCC. The preferred apparatus is a high-speed countercurrent chromatographic centrifuge having a multilayer-coil separation column. The preferred motion is planetary motion (either coaxial or eccentric). Particularly preferred is synchronous planetary motion in which the number of revolutions about each of the two axes of rotation is the same within a particular period of time. The synchronous planetary motion provided by the centrifuge performs two functions. First, the synchronous rotation of the column holder constantly unwinds the twist of the flow tubes caused by revolution. This permits continuous elution through the rotating coil without the use of a conventional rotary seal device, which can be a potential source of leakage and contamination of collected fractions. Additionally, when the coiled column is coaxially mounted about the coil holder, the planetary motion of the holder unilaterally distributes two solvent phases in the column in such a way that one phase occupies the head side, and the other phase occupies the tail side of the coil. This head-tail relationship refers to the Archimedean screw force acting on the rotating coil, where all objects of different density are driven from the tail portion of the coil toward the head of the coil. This hydrodynamic phenomenon can be utilized for performing CCC in two ways. The coil can be entirely filled with a first liquid phase and eluted with the second liquid phase from the tail toward the head. Alternatively, the coil can be filled with the second liquid phase followed by elution with the first liquid phase from the head toward the tail. In either case the hydrodynamic phenomenon facilitates rapid movement of the mobile phase through the stationary phase, yielding extremely high retention of the stationary phase in the coil.

In one group of embodiments, the present inventive method is used to separate the polar organic compounds in a compound mixture from each other using HSCCC. The term "polar organic compounds" refers throughout the specification to those organic compounds which are typically more soluble in water than in hydrophobic organic solvents. Polar organic compounds will usually have two or more functional groups on each molecule which are hydroxyl, amino, acid (e.g., carboxylic, phosphonic, sulfonic) or lower acyl (e.g., formyl, acetyl). Examples of polar organic compounds include, for example, catecholamines, carbohydrates, carbohydrates bearing protecting groups for one or more hydroxyl functionalities, other polyalcohols and polyamines, amino acids (both naturally occurring and synthetic), peptides, nucleic acids, and the like.

In this group of embodiments of the invention, two immiscible solvent phases are equilibrated relative to one another to yield a two-phase mixture. A countercurrent chromatographic centrifuge column is then charged with a first liquid phase of the mixture. The first liquid phase is charged with a ligand, and the compound mixture containing the polar organic compounds to be separated is introduced into the column. Alternatively, the ligand is added to the stationary phase (first liquid phase) prior to its introduction to the column. The centrifuge is started and the second liquid phase, or mobile phase, is passed through the column. Fractions containing the various components of the mixture are eluted, collected and identified.

The liquid phases are each independently an organic phase or an aqueous phase. In a preferred embodiment, the first liquid phase is an organic phase and the second liquid phase is an aqueous phase. In a further preferred embodiment, the first liquid phase is an organic phase and the second liquid phase is an acidic aqueous phase.

As noted above, the ligand is typically selected so that it is retained primarily in the first liquid phase (the stationary phase). Additionally, an appropriate ligand for affinity CCC separations is one which provides suitable partitioning of the analytes of interest into both the stationary and mobile phases. In other liquid-liquid chromatographic methods, optimization of the partition coefficient is carried out by altering either the hydrophobicity of the solvent system, or the pH. The use of a suitable ligand provides a third parameter, affinity to a complexation agent or ligand, which selectively changes the partition coefficient of a particular group of compounds. Thus, a suitable ligand is one which possesses affinity for the analytes of interest to increase the retention of those analytes in the stationary phase. In those applications in which the stationary phase is an organic phase, the ligand will be a hydrophobic compound. Still further, when separation of polar organic amines is desired, a suitable ligand for those amines will be a hydrophobic phosphoric or phosphonic acid derivative, preferably di-(2-ethylhexyl) phosphoric acid. Alternatively, hydrophobic sulfonic acids and carboxylic acids can also be used. For the separation of other polar organic compounds, such as amino acids and peptides, suitable ligands will include the above-mentioned hydrophobic acids as well as derivatized amino acids such as N-dodecanoyl-L-proline-3,5-dimethylanilide. The concentration of ligand which is used is typically from about 0.1 to about 200 mM, preferably from about 1.0 to about 100 mM, and more preferably from about 10 to about 50 mM.

The amount of a compound mixture which is to be separated into its component species will typically be from about 1 mg to about 1 kg, preferably from about 0.05 grams to about 50 grams, more preferably from about 0.5 to about 10 grams, and still more preferably from about 1.0 to about 5.0 grams.

In another group of embodiments, the present inventive method is used to separate acidic polar organic compounds of a compound mixture from each other using pH-zone-refining CCC. In this method, a ligand and an acid are added to a first liquid phase of two pre-equilibrated immiscible liquid phases. A countercurrent chromatographic centrifuge column is then charged with the first liquid phase. Base is then added to the second liquid phase of the two pre-equilibrated immiscible liquid phases to form a basic mobile phase. The compound mixture is introduced into the injection port of the countercurrent chromatographic centrifuge column and the basic mobile phase is passed through the countercurrent chromatographic centrifuge column to elute, in a separated form, the component polar organic compounds of the compound mixture.

The amount of compound mixture which can be separated into its component species using this method is, as above, from about 1 mg to 1 kg quantities. Preferably, the amount to be separated is from about 0.05 to 50 grams, and more preferably from about 1.0 to about 10 grams.

As above, the liquid phases are each independently an organic phase or an aqueous phase. In a preferred embodiment, the first liquid phase is an organic phase and the second liquid phase is an aqueous phase. In a further preferred embodiment, the first liquid phase is made acidic with an organic acid which is either acetic acid, trifluoroacetic acid, propionic acid or butanoic acid. In a still further preferred embodiment, the first liquid phase is made acidic with trifluoroacetic acid. In another preferred embodiment, the second liquid phase is made basic with either ammonia or NaOH, more preferably ammonia.

The ligand used in this group of embodiments is also selected so that it is retained primarily in the first liquid phase (the stationary phase). In those applications in which the stationary phase is an organic phase, the ligand will be a hydrophobic compound, such as a derivatized amino acid, preferably N-dodecanoyl-L-proline-3,5-dimethylanilide or a phosphoric or phosphonic acid, preferably DEHPA.

In yet another group of embodiments, the present inventive method is used for separating a quantity of basic polar organic compounds of a compound mixture from each other using affinity pH-zone-refining CCC. In these embodiments, as above, two immiscible liquid phases are equilibrated relative to one another, then separated. A countercurrent chromatographic centrifuge column is charged with a first liquid phase which is made basic either prior to or following its introduction into the column. The first liquid phase is also charged with a ligand. The mixture containing a quantity of polar organic bases to be separated is then introduced into the column. The centrifuge is started and the second liquid phase, which has previously been made acidic, is passed through the column. Fractions containing the various components of the mixture are eluted, collected and identified.

As above, the liquid phases are each independently an organic phase or an aqueous phase. In a preferred embodiment, the first liquid phase is an organic phase and the second liquid phase is an aqueous phase. The liquid phases will typically be acidified or basified as required using the acids and bases described above. Additionally, the ligand used will be as described above for the polar organic acid compound mixture. In another preferred embodiment, pH-zone-refining countercurrent chromatography can be conducted on a preparative scale using 1 mg to 1 kg of the mixture containing the polar organic bases which are to be separated.

The following examples are offered by way of illustration and are not meant to limit the scope of the invention.

EXAMPLES

Examples 1–4 illustrate separations using affinity countercurrent chromatography using the apparatus and conditions provided in the sections which follow. Example 5 illustrates a separation of polar compounds using affinity CCC run in the pH-zone refining mode. The particular conditions used in that separation are provided with the example.

Apparatus

In Examples 1–4, two different types of high-speed CCC centrifuges were employed. One is a commercial semipreparative model (Ito multilayer coil separator/extractor, P.C. Inc., Potomac, Md., USA) of the coil planet centrifuge and the other is a semianalytical high-speed CCC centrifuge equipped with a set of three column holders. The latter centrifuge was fabricated at the NIH machine shop, but a comparable apparatus is available from Pharma-Tech Research Corporation, Baltimore, Md., USA was used throughout the present studies. The detailed design of the semipreparative apparatus was given elsewhere (U.S. Pat. No. 4,430,216).

The commercial semipreparative model holds a multilayer coil separation column and a counterweight symmetrically at a distance of 10 cm from the central axis of the centrifuge. The column holder is equipped with a plastic planetary gear which is engaged to an identical stationary sun gear mounted around the central axis of the apparatus. This gear arrangement produces the desired planetary motion to the column holder, i.e. rotation about its own axis and revolution around the centrifuge axis in the same direction at the same rate. This planetary motion also prevents the flow tubes from twisting during revolution, thus permitting the elution of the mobile phase through the column without the use of rotary seals.

The separation column consists of a single piece of 1.6 mm ID, 160 m long Tefzel tubing (Zeus Industrial Products, Orangeburg, S.C., USA) wound around the column holder hub with 16 layers and 325 mL capacity. Each terminal of the column was connected to a flow tube (0.85 mm ID PTFE) (Zeus Industrial Products) by the aid of a set of tube connectors (Upchurch Scientific Co., Oak Harbor, Wash., USA) which were rigidly mounted on the holder flange. A narrow-bore PTFE tube (0.3 mm ID×5 m) (Zeus Industrial Products) was placed at the outlet of the column to stabilize the effluent flow, thus facilitating the recording the elution curves.

The semianalytical high-speed CCC centrifuge is equipped with a set of three column holders held at a distance of 7.6 cm from the centrifuge axis. This design provides a further advantage in that the multilayer coiled columns are balanced around the axis and no counterweight is necessary. Each column consists of 11 layers of coils that are made of 0.85 mm ID PTFE (polytetrafluoroethylene) tubing (Zeus Industrial Products). The three columns are connected in series on the rotary frame to provide a total capacity of 180 mL. A column revolution of 1000 rpm (~84×g at the column holder axis) was applied.

The speed of the apparatus was regulated with a speed controller (Bodine Electric Company, North Chicago, Ill., USA).

Reagents

Methanol was glass-distilled chromatographic grade (Baxter Healthcare Corporation, Muskegon, Mich., USA). HPLC grade of hexane and ethyl acetate, and reagent grade of sodium hydroxide and hydrochloric acid were purchased from Fisher Scientific Company (Fair Lawn, N.J., USA). Dinitrobenzoyl(DNB)-leucine, DNB-phenylglycine and 3,5-DNB chloride were obtained from Aldrich Chemical Co., (Milwaukee, Wis., USA). DL-proline, DL-valine, DL-phenylalanine, 2-ethoxy-1-ethoxycarbonyl-1,2-dihydrofuran (EEDQ), dodecanoyl chloride, 3,5-dimethylaniline were purchased from Spectrum Chemical Mfg. Corp. (New Brunswick, N.J., USA). Methyl t-butyl ether (HPLC grade), ammonium acetate (reagent grade) and hydrochloric acid (reagent grade) were purchased from Fisher Scientific Company. Di-(2-ethylhexyl)phosphoric acid (DEHPA), the eight dipeptides and the DNP-amino acids were obtained from Sigma Chemical Company, St. Louis, Mo., USA. Other analytes including DL-dopa (97%), epinephrine (95%), norepinephrine hydrochloride (99%), normetanephrine hydrochloride (99%), hydroxytyramine hydrochloride (98%) and tyramine hydrochloride (98%) were all from Aldrich Chemical Company.

Synthesis of N-dodecanoyl-L-proline-3,5-dimethylanilide

N-dodecanoyl-L-proline: L-proline (11.6 g, 0.1 mol) was dissolved in 150 mL of 1M NaOH solution and cooled in an ice both. To this solution dodecanoyl chloride (24.1 g or 0.11 mol) and 200 mL of 1M NaOH solution were added simultaneously over a period of 20 min. The solution was stirred at room temperature for 45 min and acidified with concentrated HCl (pH 2–3). The solution was extracted with diethyl ether and the organic phase was washed with 12% NaCl solution. The organic phase was then dried over sodium sulfate and evaporated to provide 30 g of N-dodecanoyl-L-proline as an oil (100% yield) which was carried on without purification.

N-dodecanoyl-L-proline-3,5-dimethylanilide: To 400 mL of a THF solution containing 13.0 g (0.11 mol) of freshly distilled 3,5-dimethylaniline and 30 g (0.1 mol) of N-dodecanoyl-L-proline, was added 200 mL of THF containing 25.2 g (0.1 mol) of EEDQ at room temperature. The mixture was kept at room temperature for 24 hr and the solvent was evaporated. The residue was redissolved in dichloromethane and washed with 1% orthophosphoric acid, 0.2M NaOH and then distilled water. The resulting solution was dried over sodium sulfate, filtered and evaporated. Recrystallization of the residue from ethanol-water gave 35.0 g (87% yield) of white solid.

Synthesis of Analytes (±) N-(3,5-dinitrobenzoyl)amino acids: An appropriate amount of racemic amino acid (23 mmol) was dissolved in 50 mL of 1M NaOH solution and cooled in an ice-bath. To this solution 3,5-dinitrobenzoyl chloride (5.3 g, 23 mmol) and 50 mL of 1M NaOH solution were added simultaneously over a period of 20 min. The resulting solution was stirred at room temperature for 90 min and acidified with concentrated HCl (pH 2–3). The resulting solid was collected by filtration and washed with water. Recrystallization of the solid from ethanol-water gave the corresponding DNB-amino acid.

Preparation of Solvent Phases and Sample Solutions

Each solvent system was prepared by equilibrating the solvent mixture, excluding the ligand, in a separatory funnel at room temperature. After two clear layers were formed, the two phases were separated. Then, a desired amount of the ligand was added to the organic phase which was then used as the stationary phase. The aqueous phase was used as the mobile phase. The composition of the two-phase solvent systems used in the present studies are listed in Table 1 together with partition coefficients of the applied samples.

Partition coefficients were measured using the standard test tube procedure as follows: The two-phase solvent system was prepared as described above. An aliquot of 2 mL of each phase, a total of 4 mL, was delivered in a test tube (13 mm ID×100 mm length) where a desired amount of the ligand and 1–2 mg of sample were added. Then, the test tube was stoppered and the contents were mixed until the resolved sample was completely equilibrated between two phases. Using a vortex mixer, it required 10 successive applications at a few second intervals after the sample was dissolved in the solvent. The tube was stand still until clear two layers were formed. If necessary, the tubes were centrifuged for 2–3 min at 1000×g to accelerate the phase separation. An aliquot of each phase, usually 100 µl, was separately diluted with 2 mL of a suitable diluent, usually methanol, and the absorbance determined with a spectrophotometer, (Zeiss, Hanover, Md., USA) at a desired wavelength. The partition coefficient for each component was obtained by the absorbance of the upper phase divided by that of the lower phase.

The partition coefficients are also measured from the chromatogram using the following equation:

$$K=(V_R-V_m)/(V_c-V_m) \quad (1)$$

where $V_R$, $V_m$ and $V_c$ indicate retention volume of the analyte, mobile phase volume in the column and total column capacity, respectively.

TABLE 1

Two-Phase Solvent Systems and Partition Coefficient (K) Values of Mixture Components

| Solvent Systems | | Ligand | Sample Components | K |
|---|---|---|---|---|
| 8: | Hexane | DPA | (−)-DNB-Val | 0.35 |
| 2: | Ethyl Acetate | (1.6 g per | (+)-DNB-Val | 0.87 |
| 5: | Methanol | 80 mL) | (−)-DNB-Phg | 0.41 |
| 5: | 10 mM HCl | | (+)-DNB-Phg | 0.87 |
| | | | (−)-DNB-Phe | 0.53 |
| | | | (+)-DNB-Phe | 1.57 |
| | | | (−)-DNB-Leu | 0.66 |
| | | | (+)-DNB-Leu | 2.87 |
| 1: | Methyl t-Butyl Ether | DEHPA | DOPA | 0.01 |
| 1: | 0.1 M NH$_4$OAc and | 1.5% | Epinephrine | 0.4 |
| | 0.5 M HCl | | Normetanephrine | 0.5 |
| | | | Dopamine | 0.8 |
| | | | Tyramine | 1.7 |
| 1: | Methyl t-Butyl Ether | DEHPA | Gly—Tyr | 0.1 |
| 1: | 0.1 M KH$_2$PO$_4$ | 10% | Tyr—Gly | 0.2 |
| | | | Ala—Tyr | 0.5 |
| | | | Tyr—Ala | 0.8 |
| | | | Val—Tyr | 2.8 |
| | | | Tyr—Val | 4.9 |
| | | | Leu—Tyr | 10 |
| | | | Tyr—Leu | 18 |

The sample solutions were prepared by dissolving the sample mixture (0.1–10 mg of each component) in 1–2 mL of the solvent used for separation.

Separation Procedure

The CCC separations were performed as follows: The column was first entirely filled with the organic stationary phase. Two different methods were used. In the first method the column was entirely filled with the organic phase containing the ligand. This simple method results in continuous elution of the ligand in the effluent, although it may not affect the separation. This complication is eliminated in the second method as follows: A proper amount of ligand-free stationary phase was first pumped into the column followed by the known volume of the ligand-containing stationary phase (200 mL for the 1.6 mm ID column and 80 mL for the 0.85 mm ID column) by discharging an excess amount of the ligand-free stationary phase from the outlet of the column. During the elution, a small amount of ligand-free stationary phase remaining at the end of the column absorbs the carried-over ligand from the flowing mobile phase.

After the column was filled with the stationary phase, the mobile phase was pumped into the head of the column at a suitable flow rate (3.3 mL/min for 1.6 mm ID column and 1 mL/min for 0.85 mm ID column), while the column was rotated at a desired rate. After the mobile phase front emerged from the column, the run was continued until the polar impurities in the ligand were eluted and the uv trace returned to the base line. Then, the sample solution was injected through the sample port. When the ligand contains no impurity, however, this preequilibrium procedure is not required and the sample injection may be made immediately after filling the column with the stationary phase. The effluent was continuously monitored through a uv monitor (Uvicard S, LKB Instruments, Bromma, Stockholm, Sweden) at 254 or 280 nm and collected into test tubes at 2 min intervals using a fraction collector (Ultroracol LKB Instruments).

The separations can be repeated, if necessary, by injecting the sample in succession without renewing the stationary phase, as is routinely practiced in high performance liquid chromatography (HPLC). The blank run for each separation was performed using ligand-free stationary phase but under the otherwise identical experimental conditions.

EXAMPLE 1

This example illustrates the separation of a mixture of four different DNB-amino acid racemates.

Figure 1A:
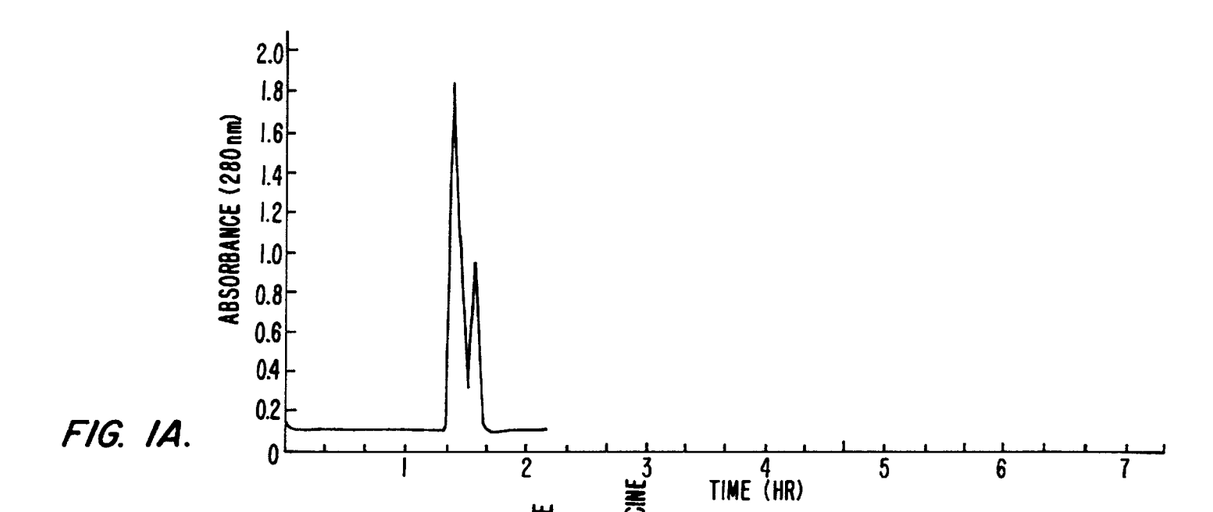
In FIG. 1A, no ligand was used in the stationary phase.
Figure 1B:
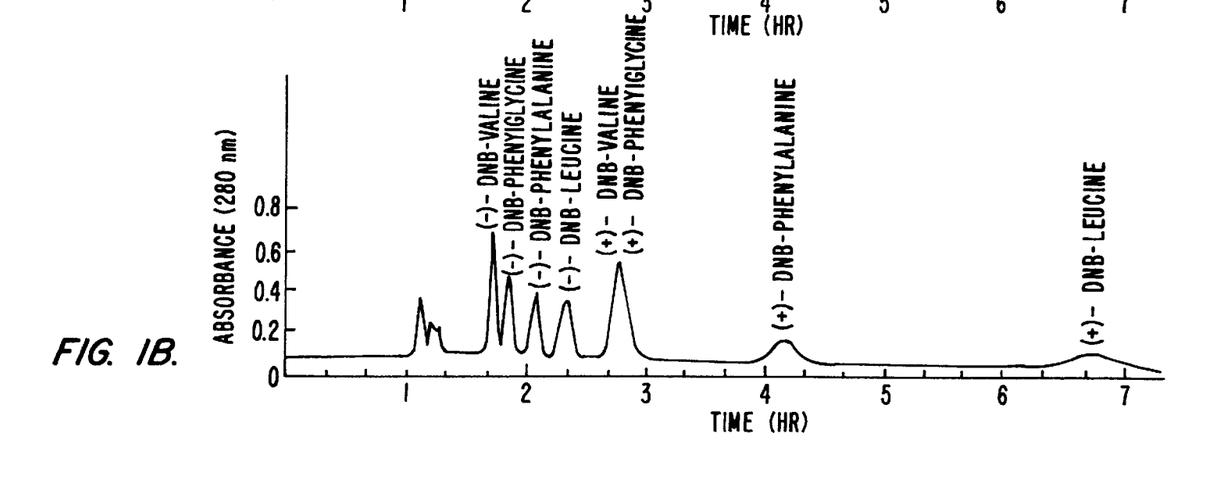
In FIG. 1B, DPA (N-dodecanoyl-L-proline-3,5-dimethylanilide; 1.6 g/80 mL) was added to the stationary phase as a ligand.

A mixture of DNB-amino acid racemates was prepared which included DNB-valine, DNB-leucine, DNB-phenylalanine and DNB-phenylglycine (10 mg of each racemate). The mixture was subjected to separation as described above, both in the presence and absence of an added ligand. The separations were performed with a solvent system composed of hexane/ethyl acetate/methanol/10 mM HCl (8:2:5:5, v/v) using the semianalytical high-speed CCC unit (operating at 1000 rpm) and a flow rate of 1 mL/min. With a ligand-free solvent system, all components were eluted together close to the solvent front forming two partially resolved peaks (see FIG. 1A). When a ligand, DPA (N-dodecanoyl-L-proline-3,5-dimethylanilide), was added to the stationary phase (1.6 g/80 mL)(see FIG. 1B), all components were retained longer in the column and well separated from impurities eluting near the solvent front. The four (−)-enantiomer peaks are well resolved followed by elution of the (+)-enantiomers. As can be seen in FIG. 1B, the valine and phenylglycine derivatives eluted together as a single peak due to the same partition coefficient in the present solvent system. The separation was completed in slightly over 7 hours.

EXAMPLE 2

This example illustrates the separation of five DNP (dinitrophenyl)amino acids.

Figure 2A:
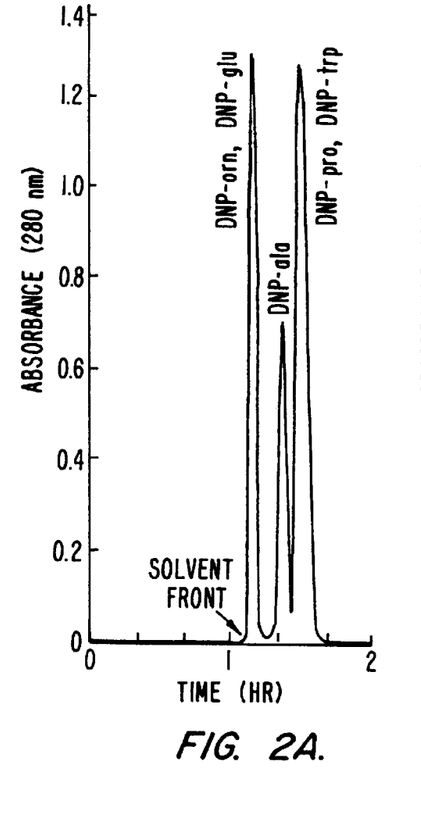
FIG. 2 shows two HPLC chromatograms from separations of five DNP-amino acids using affinity HSCCC.
Figure 2B:
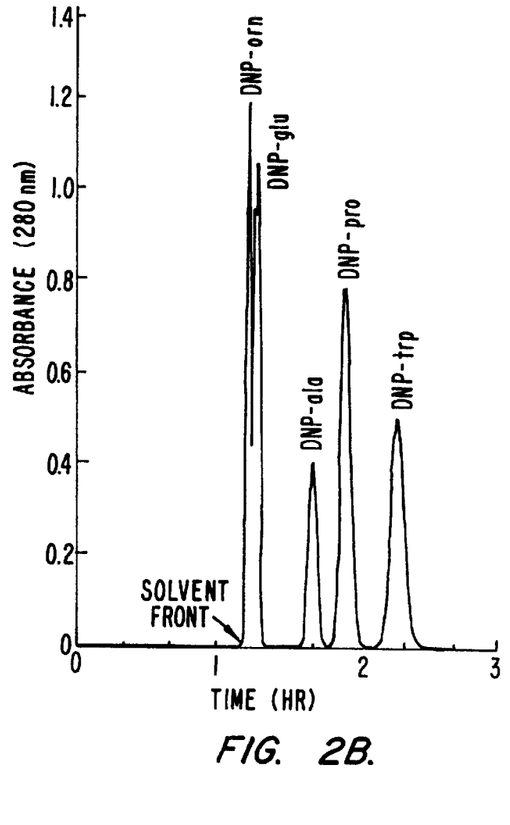

A sample mixture of DNP-L-Orn, DNP-DL-Glu, DNP-L-Ala, DNP-L-Pro and DNP-L-Trp (2 mg each, available from Sigma Chemical Company, St. Louis, Mo., USA) was prepared and chromatographed as described for the protected amino acids in Example 1. An initial separation was carried out in the absence of added DPA (see FIG. 2A) and the five components were eluted in three peaks where the resolution between the second and third peaks was incomplete. The separation was substantially improved by adding DPA (1.6 g/80 mL) in the stationary phase as shown in FIG. 2B. The first peak was partially resolved into two peaks while the second and third peaks were completely separated into three peaks. The separation time was 2.5 hours.

EXAMPLE 3

This example illustrates the separation of eight isomeric dipeptides.

Four pairs of isomeric dipeptides (Gly-Tyr, Tyr-Gly, Ala-Tyr, Tyr-Ala, Val-Tyr, Tyr-Val, Leu-Tyr, Tyr-Leu) all containing a tyrosine moiety were selected as samples due to their convenient detection by uv at 280 nm. A mixture of 5 mg of each dipeptide was prepared as the sample. These polar peptides are usually separated by CCC using n-butanol/water systems with high viscosity and low interfacial tension which may produce relatively lower retention in high-speed CCC. All these peptides exhibit extremely low partition coefficient in a ligand-free methyl t-butyl/phosphate buffer system. However, introduction of ligand to the system improves the partition coefficient as shown in Table 1.

Figure 4A:
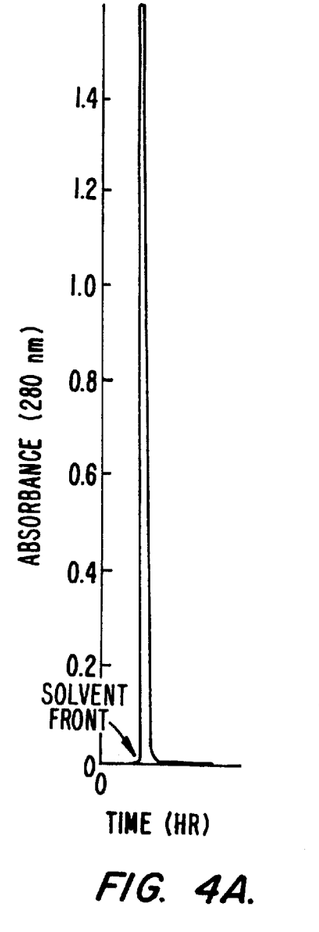
FIG. 4 shows two HPLC chromatograms from separations of five catecholamines using affinity HSCCC.
Figure 4B:
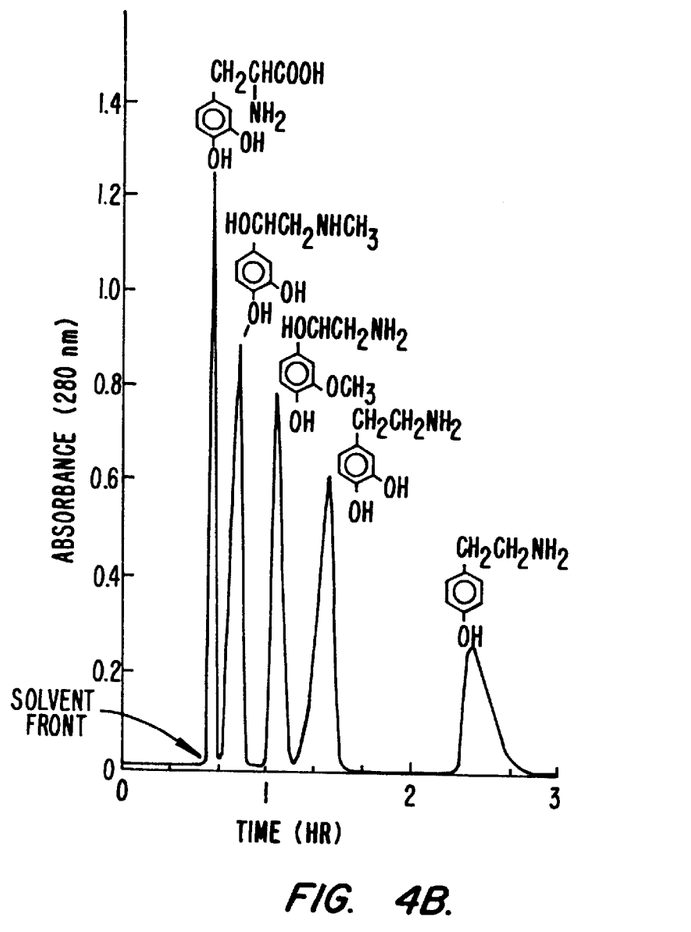

Separation of the dipeptide mixture was carried out using a semipreparative column and a flow rate of 3.3 mL/min at 800 rpm. FIG. 4 shows the chromatogram obtained from a solvent system composed of methyl t-butyl ether/0.1M potassium phosphate buffer (1:1). In order to accelerate the elution of hydrophobic groups, dilute HCl was added to the mobile phase, first at a concentration of 0.035M after one hour and then at 0.1M one more hour later. Because of small partition coefficients of glycine derivatives are only partially resolved and eluted shortly after the solvent front. The rest of the peptides were well resolved except for two valine derivatives.

EXAMPLE 4

This example illustrates the separation of catecholamines.

Figure 3A:
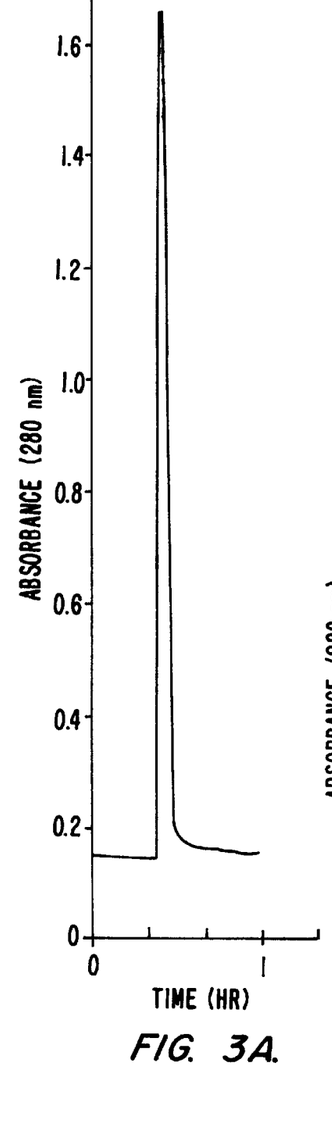
FIG. 3 shows two HPLC chromatograms from separations of four isomeric pairs of dipeptides using affinity HSCCC.
Figure 3B:
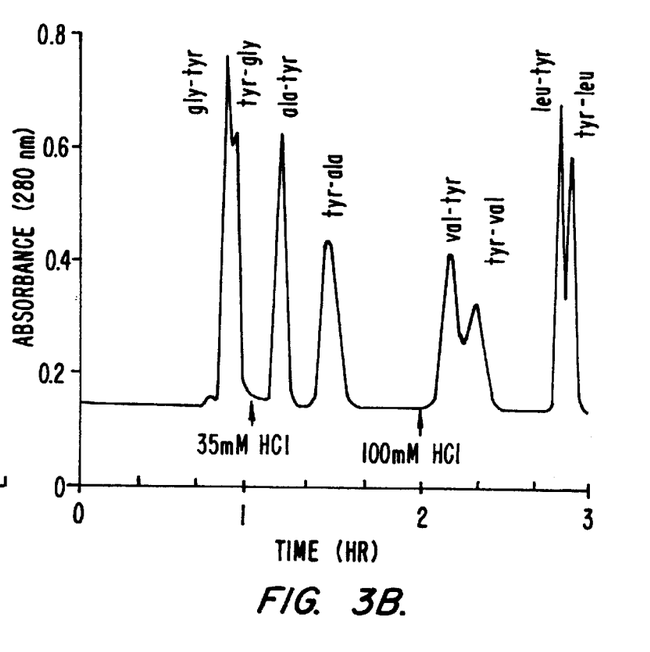

A mixture of polar catecholamines (L-Dopa, epinephrine, normetanephrine, dopamine and tyramine; 5 mg each) was prepared. Polar catecholamines such as epinephrine partition almost exclusively into the aqueous phase even in the n-butanol/water two-phase solvent systems. Consequently, suitable partition coefficients are usually only obtained by saturating the aqueous phase with a salt such as barium chloride (see, Weisz, et al., *J. Chromatogr.* 384:132–136 (1987)). The use of a ligand such as DEHPA (di-(2-ethylhexyl)phosphoric acid alleviates this problem as shown in Table 1. Separation of the five catecholamines was obtained using the semi-preparative high-speed CCC unit. The separation was performed with a two-phase solvent system composed of methyl t-butyl ether and the same volume of an aqueous phase containing both ammonium acetate (0.1M) and HCl (0.05M) at a flow rate of 3.3 mL/min and 800 rpm. In the absence of the ligand (see FIG. 3A), all components eluted at the solvent front as a single peak. With DEHPA (1.5%, v/v) in the stationary phase (see FIG. 3B), however, all components were completely resolved according to their K values shown in Table 1. Although these catecholamines are unstable in a basic solution, the present mobile phase elutes them as stable HCl salts at an acidic pH.

EXAMPLE 5

This example illustrates the separation of a group of catecholamines using a pH-zone refining mode of affinity countercurrent chromatography with DEHPA as the ligand in the stationary phase.

Selection of Solvent System

The selection of solvent system which is suitable for separating the components in a mixture involves an initial determination of partition coefficients of the analyte components in the solvent system. Table 2 provides the partition coefficients for six analytes in seven different two-phase solvent systems.

TABLE 2

Partition Coefficients of Catecholamines in Seven Different Solvent Systems

| Analyte | Solvent System | | | | | | |
|---|---|---|---|---|---|---|---|
| | I | II | III | IV | V | VI | VII |
| DOPA | 0.21 | 0.06 | <0.01 | <0.01 | 0.15 | 0.02 | 0.12 |
| Epinephrine | 0.24 | 0.13 | 0.06 | 0.16 | 5.83 | 0.01 | 1.42 |
| Norepinephrine | 0.20 | 0.10 | 0.04 | <0.01 | 6.12 | 0.01 | 1.80 |
| Normetanephrine | 0.27 | 0.18 | <0.01 | 0.02 | 13.0 | 0.02 | 2.84 |
| Dopamine | 0.44 | 0.18 | 0.08 | 0.01 | 19.3 | 0.03 | 7.19 |
| Tyramine | 0.18 | 0.39 | <0.01 | 0.02 | 21.3 | 0.08 | 9.76 |

Solvent systems: I, n-Butanol/H$_2$O; II, n-Butanol/0.1M NH$_4$OAc; III, MBE/H$_2$O; IV, MBE/0.1M NH$_4$OAc; V, MBE/DEHPA/0.1M NH$_4$OAc (9:1:10); VI, MBE/DEHPA/0.05M HCl (9:1:10); VII, MBE/DEHPA/0.1M NH$_4$OAc & 0.05M HCl (9:1:10).

As can be seen in Table 2, all analytes predominantly partition into the aqueous phase even in the hydrophilic solvent systems such as n-butanol/water and n-butanol/0.1M ammonium acetate (1:1) (Solvents I and II in Table 2).

Additionally, catecholamines are unstable under basic conditions and basic reagents such as ammonia and triethylamine can not be used as a retainer in the solvent system. This problem is overcome by introducing a ligand such as DEHPA in the organic stationary phase. In ligand-free solvent systems III (MBE/water) and IV (MBE/ammonium acetate), the analytes favored partition to the aqueous phase throughout the applicable pH range. With the presence of the ligand however, all 5 catecholamines predominantly partitioned into the stationary phase under the neutral condition (solvent system V) and into the aqueous phase under the acidic condition (solvent system VI), while the ligand was almost unilaterally distributed into the organic phase because of its high K value (>100).

In brief, the introduction of the ligand in the stationary phase provided an ideal solvent system for pH-zone-refining CCC of polar catecholamines by using ammonium acetate as a retainer salt and hydrochloric acid as an eluent acid.

The CCC apparatus used was a commercial model (Ito Multilayer Coil Separator/Extractor) as described above. The separation column used was prepared by winding a single piece of 1.6 mm ID, 160 m long Tefzel tubing (Zeus Industrial Products, Orangeburg, S.C., USA) around the column holder hub making 16 layers with a 315 mL capacity. The speed of the apparatus was regulated and held at an optimum speed of 800 rpm with a speed controller (Bodine Electric Company, North Chicago, Ill., USA).

The solvent phases were prepared by mixing about equal volumes of methyl tert-butyl ether and distilled water in a separatory funnel until they were thoroughly equilibrated. The phases were separated and DEHPA (20%, v/v) and ammonium acetate (200 mM) were added to the upper organic stationary phase. The lower aqueous phase was acidified with hydrochloric acid (50 mM) and used as the mobile phase.

The sample solution was prepared by dissolving a sample mixture (500 mg each of DL-Dopa, epinephrine, norepinephrine hydrochloride, normetanephrine hydrochloride, hydroxytyramine hydrochloride and tyramine hydrochloride) in 40 mL of the aqueous phase, to which 4 mL of 1M HCl had been added.

The column was entirely filled with the organic phase and the sample mixture was injected through the sample port. The mobile acidic aqueous phase was pumped into the inlet of the column at a flow rate of 3.3 mL/min in the head to tail elution mode, while the column was rotated at 800 rpm. The effluent from the outlet of the column was continuously monitored with a uv monitor (Uvicord S, LKB Instruments, Bromma/Stockholm, Sweden) at 280 nm and collected into test tubes at two minute intervals (6.6 mL/tube) using a fraction collector (Ultrorac, LKB Instruments). After the desired peaks were eluted, the apparatus was stopped and the column contents were collected into a graduated cylinder to determine the retention of the stationary phase, relative to the total column capacity.

The collected fractions were analyzed for content and the pH value of each fraction was also determined (using a portable pH meter from Accumet Portable Laboratory, Fisher Scientific Co., Pittsburgh, Pa., USA). The catecholamines were identified by their partition coefficient, $K_{std}$, in a standard two-phase system composed of methyl tert-butyl ether/DEHPA/aqueous solution (9:1:10) containing ammonium acetate (0.1M) and HCl (0.05M). An aliquot of each fraction (0.1 mL) was combined with 2 mL of the standard solvent system in a test tube and vigorously shaken to equilibrate the solute with the solvents. After the two layers separated, 0.1 mL of each phase was diluted with 2 mL of methanol and the absorbance was determined at 430 nm. The standard partition coefficient ($K_{std}$) was obtained by dividing the absorbance value of the upper phase by that of the lower phase. The analytes in each pH zone were also identified by NMR spectroscopy.

Figure 5:
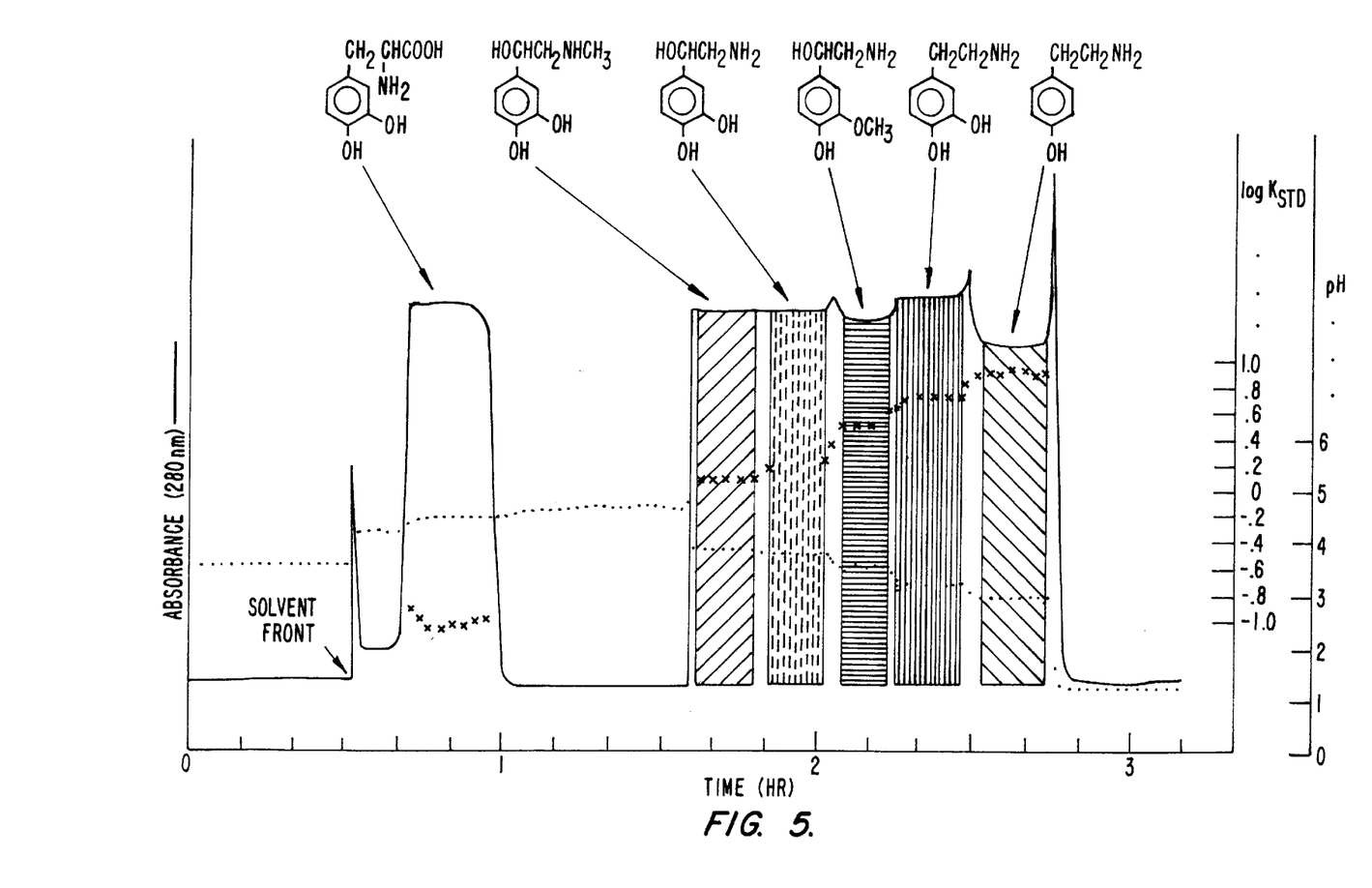
FIG. 5 shows a chromatogram from a pH-zone-refining affinity CCC separation of six components: one amino acid and five catecholamines (each 500 mg).

FIG. 5 provides the results of the separation of one amino acid (DL-Dopa) and five catecholamines. In the uv tracing (solid line), all catecholamines were eluted as highly concentrated fused rectangular peaks associated with sharp impurity peaks at their borders. The pH-curve of the fractions (dotted line) reveals a succession of plateaus in a downward stair case fashion. Each zone represents a specific pH that corresponds to the $pK_a$ and the hydrophobicity of the analyte. The log $K_{std}$ line (xxxx) further indicates sharp borders of each zone with minimum overlap. Dopa was eluted much earlier than the major peaks because it exists in zwitterionic form with an extremely low K value as indicated in Table 1.

As these results illustrate, the use of a ligand in the stationary phase will significantly extend the domain of applications for pH-zone refining CCC.

The above description is illustrative and not restrictive. Many variations of the invention will become apparent to those of skill in the art upon review of this disclosure. Merely by way of example a variety of analytes, ligands, liquid phases and mixtures, and other materials may be used without departing from the scope of the invention. The scope of the invention should, therefore, be determined not with reference to the above description, but instead should be determined with reference to the appended claims along with their full scope of equivalents.

All publications, patents and patent applications mentioned in this specification are herein incorporated by reference into the specification to the same extent as if each individual publication, patent or patent application was specifically and individually indicated to be incorporated herein by reference.

What is claimed is:

1. A method for separating a quantity of polar organic compounds of a compound mixture from each other using affinity high speed countercurrent chromatography, comprising:

(a) adding a ligand to a first liquid phase of two pre-equilibrated immiscible liquid phases and charging a high speed countercurrent chromatographic centrifuge column with said first liquid phase, thereby producing a high speed countercurrent chromatographic centrifuge column charged with said ligand and said first liquid phase;

(b) introducing said compound mixture into said high speed countercurrent chromatographic centrifuge column thus charged with said ligand and said first liquid phase; and (c) passing a second liquid phase through said high speed countercurrent chromatographic centrifuge column thus charged with said mixture, said ligand and said first liquid phase, to separate and elute said polar organic compounds from said high speed countercurrent chromatographic centrifuge column, wherein said quantity is from 1 mg to 1 kg.

2. The method in accordance with claim 1 wherein said first liquid phase is an organic phase and said second liquid phase is an aqueous phase.

3. The method in accordance with claim 1 wherein said first liquid phase is an organic phase and said second liquid phase is an acidic aqueous phase.

4. The method in accordance with claim 1 wherein said first liquid phase is an aqueous phase and said second liquid phase is an organic phase.

5. The method in accordance with claim 1 wherein said ligand is N-dodecanoyl-L-proline-3,5-dimethylanilide.

6. The method in accordance with claim 1 wherein said ligand is di-(2-ethylhexyl) phosphoric acid.

7. The method in accordance with claim 1 wherein each of said polar organic compounds contains at least one hydroxyl group.

8. The method in accordance with claim 1 wherein each of said polar organic compounds contains at least one amino group.

9. The method in accordance with claim 1 wherein said ligand is present in said first liquid phase at a concentration of from 0.1 to 200 mM.

* * * * *